United States Patent
Valentine

(10) Patent No.: US 8,950,251 B2
(45) Date of Patent: Feb. 10, 2015

(54) TRACER METHOD TO ESTIMATE RATES OF METHANE GENERATION THROUGH AUGMENTATION OR BIOSTIMULATION OF THE SUB-SURFACE

(75) Inventor: David Valentine, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 457 days.

(21) Appl. No.: 13/264,736

(22) PCT Filed: Apr. 23, 2010

(86) PCT No.: PCT/US2010/032236
§ 371 (c)(1),
(2), (4) Date: Oct. 14, 2011

(87) PCT Pub. No.: WO2010/124208
PCT Pub. Date: Oct. 28, 2010

(65) Prior Publication Data
US 2012/0036923 A1      Feb. 16, 2012

Related U.S. Application Data

(60) Provisional application No. 61/172,217, filed on Apr. 23, 2009.

(51) Int. Cl.
*E21B 49/00*     (2006.01)
*G01N 33/22*     (2006.01)

(52) U.S. Cl.
CPC .................. *G01N 33/225* (2013.01)
USPC ........................................ 73/152.02

(58) Field of Classification Search
CPC ................................... G01N 33/225
USPC .............. 73/152.02, 152.39, 152.42
See application file for complete search history.

(56) References Cited

U.S. PATENT DOCUMENTS 3,888,974 A * 6/1975 Stevens ...................... 423/580.2
4,139,439 A * 2/1979 Manuccia et al. ............ 204/164
(Continued)

OTHER PUBLICATIONS

International Search Report mailed Jul. 6, 2010, International application No. PCT/US10/32236, International filing date Apr. 23, 2010.
(Continued)

*Primary Examiner* — Daniel S Larkin
(74) *Attorney, Agent, or Firm* — Gates & Cooper LLP

(57) ABSTRACT

A method for determining the flux of methane newly generated through manipulation of a sub-surface environment. The method comprises: (a) measuring a baseline isotope ratio ($R_{rm}$) in methane pre-existing in the reservoir; (b) manipulating the reservoir to facilitate biogenic production of new methane in the reservoir; (c) injecting a substance labeled with the isotope into the reservoir; (d) measuring a flux ($F_m$) and isotope ratio ($R_{pm}$) of methane from the reservoir; (e) measuring an isotope ratio ($R_{pw}$) of a methane precursor in a liquid or vapor sample at one or more time periods; and (f) calculating a flux ($F_{nm}$) of the new methane from the reservoir according to an isotope mass balance, such as wherein α=isotope fractionation factor between the methane pre-cursor and the new methane.

20 Claims, 3 Drawing Sheets

(56) References Cited

U.S. PATENT DOCUMENTS

| | | | |
|---|---|---|---|
| 5,049,743 | A | 9/1991 | Taylor et al. |
| 5,388,456 | A * | 2/1995 | Kettel ................... 73/152.02 |
| 5,525,322 | A * | 6/1996 | Willms ................... 423/653 |
| 6,632,367 | B1 * | 10/2003 | Furlong et al. ................. 210/673 |
| 7,704,746 | B1 * | 4/2010 | White et al. ..................... 436/56 |
| 7,923,261 | B2 * | 4/2011 | Colle ............................ 436/172 |
| 2004/0033557 | A1 * | 2/2004 | Scott et al. ...................... 435/42 |
| 2007/0251146 | A1 | 11/2007 | Larter et al. |
| 2008/0099241 | A1 | 5/2008 | Ibrahim et al. |
| 2009/0017550 | A1 | 1/2009 | Colle |

OTHER PUBLICATIONS

Adams, C. et al., "Pure-culture growth of fermentative bacteria, facilitated by $H_2$ removal: bioenergetics and $H_2$ production," Applied and Environmental Microbiology, Feb. 2006, vol. 72, No. 2, p. 1079-1085.

Campbell, B. et al., "Hydrogen isotopic fractionation in lipid biosynthesis by $H_2$-consuming Desulfobacterium autotrophicum," Geochimica et Cosmochimica Acta (2009).

Chidthaisong, A. et al., "A comparison of isotope fractionation of carbon and hydrogen from paddy field rice roots and soil bacterial enrichments during $CO_2/H_2$ methanogenesis," Geochimica et Cosmochimica Acta, vol. 66, No. 6, pp. 983-995, 2002.

Kessler, J. et al., "A survey of methan isotope abundance ($^{14}C$, $^{13}C$, $^2H$) from five nearshore marine basins that reveals unusual radiocarbon levels in subsurface waters,".

Kinnaman, F. et al., "Carbon and hydrogen isotope fractionation associated with the aerobic microbial oxidation of methane, ethane, propane and butane," Geochimica et Cosmochimica Acta 71 (2007) 271-283.

Redmond, M. et al., "Stable isotopes in microbial ecology," Encyclopedia of Microbiology, pp. 281-285 Oxford: Elsevier, 2009.

Valentine, D. et al., "Biogeochemical investigations of marine methane seeps, Hydrate Ridge, Oregon," Journal of Geophysical Research, vol. 110, 2005.

Valentine, D. et al., "Carbon and hydrogen isotope fractionation by moderately thermophilic methanogens," Geochimica et Costmochimica Acta, vol. 68, No. 7, pp. 1571-1590, 2004.

Valentine, D. et al., "Hydrogen isotope fractionation during $H_2/CO_2$ acetogenesis: hydrogen utilization efficiency and the origin of lipid-bound hydrogen," Geobiology (2004) 2, 179-188.

Ferguson, et al., "Microbial Pilot Test for the Control of Paraffin and Asphaltenes at Prudhoe Bay", Society of Petroleum Engineers, Oct. 6-9, 1996, pp. 557-564.

Kessler, J. et al., "A survey of methan isotope abundance ($^{14}C$, $^{13}C$, $^2H$) from five nearshore marine basins that reveals unusual radiocarbon levels in subsurface waters," vol. 113, (2008).

* cited by examiner

TRACER METHOD TO ESTIMATE RATES OF METHANE GENERATION THROUGH AUGMENTATION OR BIOSTIMULATION OF THE SUB-SURFACE

CROSS REFERENCE TO RELATED APPLICATIONS

This application claims the benefit under 35 U.S.C. Section 119(e) of the following commonly-assigned application:

U.S. Provisional Application Ser. No. 61/172,217, filed on Apr. 23, 2009, by David Valentine, entitled "A TRACER METHOD TO ESTIMATE RATES OF METHANE GENERATION;"

which application is incorporated by reference herein.

BACKGROUND OF THE INVENTION

1. Field of the Invention

This invention relates to methods of estimating the quantity of methane generated through manipulation of a reservoir in a sub-surface environment. The invention also relates to methods of differentiating the newly generated methane from pre-existing methane in a sub-surface reservoir.

2. Background

Methane, $CH_4$, is an environmentally important greenhouse gas and an economically important fuel. Methane is produced in nature by four principle processes, biogenesis (as the end product of microbial metabolism), thermogenesis (chemical degradation of organic material at elevated temperature and pressure), geogenesis (as the result of interaction between geologic fluids with chemically reduced rocks), and ignigenesis (as a byproduct of combustion). Of the total 1.2 to $1.4 \times 10^{15}$ g of methane produced annually, the majority of this methane (likely greater than 85%) is produced biogenically.

Biogenic methane production, also referred to as methanogenesis, occurs at all temperatures between freezing and boiling. The majority of methane currently released to the atmosphere is produced near the surface, at temperatures between 0 and 50° C. Abundant $CH_4$ is also produced in environments with elevated temperatures (moderately thermal environments, defined here as having temperatures from around 50 to 130° C.), which include geothermal springs, hydrothermal vents, and waste digestors.

The most important of these moderately thermal methanogenic environments are deeply buried sediments, which are heated from below by the geothermal gradient (comprising much of the "deep biosphere"). Methane produced in subsurface environments generally migrates along the concentration gradient toward the ocean and atmosphere, often being physically or chemically trapped in the sub-surface environment. The trapping of methane allows for the buildup of a large reservoir, which acts as a major source of methane. Thus, there is a current movement in the field towards enhanced recovery of methane from reservoirs in sub-surface environments.

Several companies and scientific groups have been actively developing processes that manipulate sub-surface environments to facilitate methanogenesis or the biological production of methane. However, there is no known art dealing with methods designed specifically to assess and quantify the "new methane" generated through the facilitated methanogenesis. Furthermore, there is no known art related to methods of differentiating the newly generated methane from the methane pre-existing in the reservoir. One current approach would be to monitor the rate of total methane removal from the reservoir before and after augmentation, but many factors control this rate and attribution to any augmentation process is purely inference.

Differentiating between newly generated methane and pre-existing methane is important for companies in determining and comparing the efficacy of various methanogenesis facilitation processes to estimate the success and profitability of augmentation technologies. Distinguishing the newly generated methane is also important for the natural gas mining companies and their partners in terms of profit sharing and royalties.

Thus, there is a need for a method of estimating and quantifying methane generated through manipulation, such as augmentation or biostimulation, of a reservoir. There is also a need for a method of distinguishing newly generated methane from pre-existing methane in the reservoir. The present invention satisfies this need.

SUMMARY OF THE INVENTION

To overcome the limitations in the prior art described above, and to overcome other limitations that will become apparent upon reading and understanding the present disclosure, the present invention discloses methods of differentiating and estimating the quantity and flow rate of newly generated methane in various sub-surface environments.

Specifically, the present invention discloses a method of determining a flux of new methane generated through manipulation of a methane-containing subsurface organic deposit, comprising:

(a) measuring a baseline isotope ratio ($R_{rm}$) in methane pre-existing in the reservoir;

(b) manipulating the reservoir to facilitate biogenic production of new methane in the reservoir;

(c) injecting a substance labeled with the isotope into the reservoir;

(d) measuring a flux ($F_m$) and isotope ratio ($R_{pm}$) of methane from the reservoir;

(e) measuring an isotope ratio ($R_{pw}$) of a methane precursor in a liquid or vapor sample obtained from the reservoir at one or more periods; and (f) calculating a flux ($F_{nm}$) of the new methane from the reservoir according to an isotope mass balance, such as:

$$F_{nm} = F_m \times (R_{pm} - R_{rm})/(\alpha R_{pw} - R_{rm})$$

wherein $\alpha$=isotope fractionation factor between the methane precursor in the liquid or vapor and the new methane.

In this method, the reservoir may be manipulated through stimulation or augmentation. The augmentation may include an inoculum comprised of a methanogenic microbial community, nutrients to facilitate growth of native organisms, chemicals designed to alter or liberate microbial substrates in-situ, or physical processes designed to fracture the reservoir and enhance methanogenic substrates in-situ.

In this method, the substance labeled with the isotope may be diluted with the reservoir's contents prior to injection into the reservoir. Preferably, the isotope is an isotope naturally present in the methane, such as deuterium, tritium, carbon 13 or carbon 14. If the isotope is deuterium or tritium, the isotope is added to the reservoir as labeled water. If the isotope is carbon 13 or carbon 14, the isotope is added to the reservoir as carbon dioxide, carbonic acid, bicarbonate or carbonate ion.

BRIEF DESCRIPTION OF THE DRAWINGS

Referring now to the drawings in which like reference numbers represent corresponding parts throughout.

DETAILED DESCRIPTION OF THE INVENTION

Figure 1:
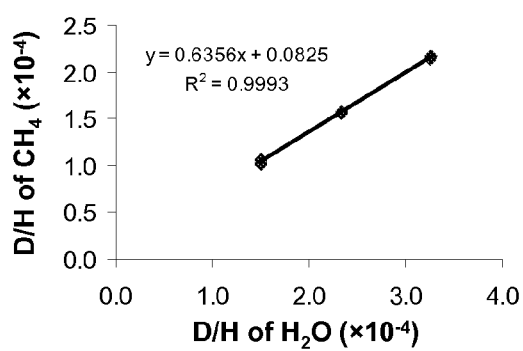
FIG. 1 is a graph depicting the linear relationship between D/H (Deuterium/Hydrogen) of environmental water and D/H of methane produced.

In the following description of the preferred embodiment, reference is made to a specific embodiment in which the invention may be practiced. It is to be understood that other embodiments may be utilized and structural changes may be made without departing from the scope of the present invention.

Overview

The present invention estimates the quantity of methane generated in various sub-surface environments through biological activity, with a particular application toward bioaugmentation or stimulation of methanogenesis in a reservoir in a sub-surface environment, including deposits of coal, peat, lignite, oil shale, oil formations, traditional black oil, viscous oil, oils sands, tar sands, asphalt volcanoes, and other sedimentary or extrusive deposits containing organic material. The present invention injects highly-deuterium labeled water or other select isotopes into sub-surface environments in combination with microbial inoculum, nutrients, or reservoir fracturing, and follows the isotopic label into newly formed methane associated with the injection. By collecting subsequent water and gas samples from the reservoir, and knowing the rate of gas removal and isotope fractionation from methanogenesis, it is possible to estimate the contribution of the augmentation to the gas removed from the ground. This is useful for assessing the success of such technologies, optimizing process control and for apportioning the profit arising from the augmentation.

Tracer Method

The process described herein is a tracer method that determines the production rate of methane arising from any of several bioaugmentation or stimulation processes applied to reservoirs in sub-surface environments. The utility of the process is in determining the contribution of methane from various augmentation processes, against a background of pre-existing methane.

This process entails five basic steps:

(1) determination of baseline isotopic concentrations for the reservoir;

(2) injection of deuterated water into the sub-surface environment in conjunction with an augmentation process, such as the injection of bacteria, nutrients, heating, and/or reservoir fracturing;

(3) monitoring of the flow rate and deuterium composition of methane gas subsequently removed from the reservoir;

(4) monitoring of water samples collected from the reservoir for their deuterium composition; and (5) calculating the "new methane" produced from the reservoir.

An accurate determination or estimation of the isotope fractionation between water and methane is also required for the specific augmentation process.

Each of these steps is described in more detail below.

Determination of Baseline Isotopic Concentrations for a Reservoir

A first step of the present invention is the determination of baseline isotopic concentrations for a reservoir. In this step, baseline samples of gas and water from the reservoir would be collected and analyzed for their deuterium concentrations, before injection of any label.

Injection of Deuterated Water into a Sub-Surface Environment in Conjunction with an Augmentation Process A second step of the present invention is the injection of deuterated water into the sub-surface environment in conjunction with an augmentation process, such as the injection of bacteria, nutrients, and or reservoir fracturing. Deuterated water, currently commercially available at a current cost of about $450 per liter, is injected into the sub-surface using common injection technologies.

The amount of deuterated water injected would depend on the estimated size and water content of the underlying reservoir. Ideally, the deuterated water (hereafter referred to as "label") would be injected concurrently with an augmentation of interest, possibly including an inoculum comprised of a methanogenic microbial community, nutrients to facilitate growth of native organisms, chemicals or enzymes designed to alter or liberate microbial substrates in-situ, or physical processes designed to fracture or heat the reservoir and enhance methanogenic substrates in-situ.

The label may be diluted with native reservoir water prior to injection in an attempt to reduce the uncertainty in, or minimize dilution of, the label after injection into the reservoir. The optimum dilution of label in the reservoir would be approximately 1 L label to 25 $m^3$ of reservoir water, with sensitivity down to approximately 1 L label to 125 $m^3$ of reservoir water, for a case where half the methane was "new methane" and the deuterium fractionation from water to methane was approximately 0.9.

Monitoring of the Flow Rate and Deuterium Composition of the Methane Gas Subsequently Removed from the Reservoir A third step of the present invention is the monitoring of the flow rate and deuterium composition of the methane gas subsequently removed from the reservoir. After injection into the reservoir, the deuterium content of the produced methane is monitored. This can be accomplished either in-line with a laser-based isotope monitoring system, or through the collection of discrete samples at regular intervals (e.g., twice daily), which are sent to a laboratory for quantification by isotope ratio mass spectrometry. The production rate of the methane is also needed, but this is measured as standard practice for any gas well.

Monitoring of Water Samples Collected from the Reservoir for their Deuterium Composition A fourth step of the present invention is the monitoring of water samples collected from the reservoir for their deuterium composition. The composition of label in the water samples, or possibly the water vapor samples, obtained from the reservoir is also monitored to track the extent of dilution of the label into the reservoir for purposes of calculating the new methane production. This is achieved either on-site with a laser-based isotope analyzer (for liquid or vapor samples), or discrete samples are collected and measured in a laboratory.

Calculating the "New Methane" Produced from the Reservoir

A fifth step of the present invention is calculating the "new methane" produced from the reservoir. The information collected in the previous steps is used to calculate the production of new methane at the well head of the reservoir for each sampling time interval using an isotope mass balance approach.

The variables are defined as follows:

$R_{pm}$=D/H (Deuterium/Hydrogen) ratio of produced methane, measured at the well head of the reservoir, $R_{rm}$=D/H ratio of reservoir methane, determined in the baseline study, $R_{nm}$=D/H ratio of new methane, calculated from produced water samples, $\alpha$=D/H isotope fractionation factor between water and methane, experimentally determined or estimated for each process, $R_{pw}$=D/H ratio of reservoir water sampled at each time point, $F_m$=Flux of methane produced from the reservoir for the time interval, measured at the well head of the reservoir, $F_{nm}$=Flux of new methane produced from the well for the time interval, and $F_{om}$=Flux of old methane produced from the well for the time interval. The complete isotope mass balance, considering both sources of methane, is:

$$F_m \times R_{pm} = F_{nm} \times R_{nm} + F_{om} \times R_{rm}$$

where $R_{nm}$ can be determined or estimated from the isotopic composition of the reservoir water ($R_{pw}$), yielding:

$$F_m \times R_{pm} = F_{nm} \times \alpha R_{pw} + F_{om} \times R_{rm}$$

Because it is also known that $F_m = F_{nm} + F_{om}$, the equation can be rearranged and $F_{om}$ substituted to yield:

$$F_{nm} = F_m \times (R_{pm} - R_{rm})/(\alpha R_{pw} - R_{rm})$$

Thus, the flux of new methane can be calculated directly as each term on the right side of the equation has been determined experimentally, estimated, or is known.

Mechanistic Insights on the Process

While the present invention is directed to a process to determine the "new methane" production, it does not consider the active mechanism in any detail. The relevant processes are complex and specific to each augmentation or stimulation technology; important aspects common to these processes are explained in the references set forth below. Nonetheless, it has been observed, and it is expected, that methane generated in sub-surface environments will contain deuterium in proportion to its environmental water, with a consistent and quantifiable offset (see FIG. 1 below). By defining the offset for each augmentation or stimulation process and measuring the isotopic composition of the water, the present invention provides a sound basis for calculating the deuterium composition of the new methane.

FIG. 1 is a graph showing the linear relationship between D/H of environmental water and D/H of methane produced through the syntrophic metabolism of butyrate (n=16). This experiment was performed by the inventor with a co-culture of *Syntrophothermus lipocalidus* and *Methanothermobacter thermautotrophicus* under defined laboratory conditions. The near-zero intercept of the line indicates that all deuterium from methane originates from water. The slope of the line indicates the fractionation factor, which is lower than for typical sub-surface environments.

Other Related Approaches

Any isotope or combination of isotopes present in methane could be used for the purposes described herein. These include one other stable isotope (carbon 13) and two radio-isotopes (carbon 14 and tritium). Tritium could be added as a water tracer, and the method described above could be applied with little to no modification.

Analyses could be performed by either radio-decay counting or through accelerator mass spectrometry, the latter of which provides greater sensitivity and could allow for relatively small quantities of tritium to be injected for this purpose.

Carbon 13 (13C) would need to be added as carbon dioxide or an equivalent species (carbonic acid, bicarbonate or carbonate), and would require monitoring of the carbon 13 in the methane and either the carbon dioxide of the produced gas, or the carbonic acid, bicarbonate or carbonate of the coexisting waters. As with deuterium this could be accomplished in-line with isotope ratio monitoring or by analyzing discrete samples by isotope ratio mass spectrometry. Carbon 13 is naturally at higher abundance than deuterium (approximately 1.1% of total carbon compared to 0.015% for deuterium), and the sensitivity would be much lower than for deuterium for the purposes described here.

Of the other related approaches, carbon 14 (14C) holds the greatest promise on account of the great sensitivity with which carbon 14 can be measured using accelerator mass spectrometry. Using carbon 14 for the process requires slight modification to the five steps as described here, and requires care not to exceed acceptable use limits:

(1) the determination of baseline isotopic concentrations for the reservoir would entail quantifying the carbon 14 content of the existing methane and of either the carbon dioxide, carbonic acid, bicarbonate or carbonate ion (collectively referred to as dissolved inorganic carbon) present in the reservoir, where the methane and carbon dioxide could be either gaseous or aqueous, and the other species are assumed to be aqueous;

(2) the injection of carbon 14 would entail injecting either carbon dioxide, carbonic acid, bicarbonate or carbonate ion into the sub-surface environment in conjunction with an augmentation process, such as the injection of bacteria, nutrients, and/or reservoir fracturing;

(3) the monitoring would entail both the flow rate of gas and carbon 14 composition of methane gas subsequently removed from the reservoir;

(4) the monitoring of samples collected from the reservoir for their carbon 14 composition could be achieved with gaseous carbon dioxide or with the following compounds collected from sampled water: carbon dioxide, carbonic acid, bicarbonate or carbonate ion; and (5) calculating the "new methane" produced from the reservoir requires modified equations.

The variables when using carbon 14 are defined as follows:

$R_{pm}$=14C/12C (carbon 12) ratio of produced methane, measured at the well head of the reservoir, $R_{rm}$=14C/12C ratio of reservoir methane, determined in the baseline study, $R_{nm}$=14C/12C ratio of new methane, calculated from produced carbon dioxide, bicarbonate or carbonate samples, $\alpha$=14C/12C isotope fractionation factor between methane and either carbon dioxide, bicarbonate or carbonate, experimentally determined or estimated for each process, $R_{pw}$=14C/12C ratio of reservoir carbon dioxide, carbonic acid, bicarbonate or carbonate sampled at each time point, $F_m$=Flux of methane produced from the reservoir for the time interval, measured at the well head of the reservoir, $F_{nm}$=Flux of new methane produced from the well for the time interval, and $F_{om}$=Flux of old methane produced from the well for the time interval. The complete isotope mass balance, considering both sources of methane, is:

$$F_m \times R_{pm} = F_{nm} \times R_{nm} + F_{om} \times R_{rm}$$

where $R_{nm}$ can be determined or estimated from the isotopic composition of either carbon dioxide, carbonic acid, bicarbonate or carbonate ($R_{pw}$), yielding:

$$F_m \times R_{pm} = F_{nm} \times \alpha R_{pw} + F_{om} \times R_{rm}$$

Because it is also known that $F_m = F_{nm} + F_{om}$, the equation can be rearranged and $F_{om}$ substituted to yield:

$$F_{nm} = F_m \times (R_{pm} - R_{rm})/(\alpha R_{pw} - R_{rm})$$

An accurate determination or estimation of the isotope fractionation between the inorganic carbon species and methane is also required for the specific augmentation process.

As with tritium, analyses could be performed by either radio-decay counting or through accelerator mass spectrometry, the latter of which provides greater sensitivity and could allow for relatively small quantities of carbon 14 to be injected for this purpose. These equations could also be used for cases where carbon 13 is used in the process, with little modification.

Thus, the flux of new methane can be calculated directly as each term on the right side of the equation has been determined experimentally, estimated, or is known.

One additional approach could be used in the case where the specific augmentation process led to an isotope fractionation significantly greater than fractionation between existing methane precursor material and reservoir methane. In this case, the same numerical approach could be applied, but without the injection of label into the reservoir.

BEST WAY OF PRACTICING THE INVENTION

The process of the present invention is best practiced in conjunction with any augmentation or stimulation technology.

The deuterated water or other tracer may be injected into the augmented well using any number of common technologies. The most effective route is to dilute the tracer with reservoir water and re-inject the diluted solution along with the augmentation (organisms and or nutrients). Alternatively, the tracer can be injected during reservoir fracturing, with the exact method of injection depending on the fracturing technology employed (wet vs. dry fracturing, for example).

Once the injection is completed, and the well brought back on-line, the isotopic content of the methane coming from the well, and the isotopic content of sub-surface water samples, is monitored. The optimal monitoring technology would involve in-line laser-based monitors (a water deuterium monitor and methane 13C monitor are commercially available, with methane deuterium monitors in development), but samples could also be collected regularly for isotope ratio mass spectrometry, radio-decay counting or accelerator mass spectrometry.

The proportion of "new methane" in the gas stream exiting the well bore is calculated for each time point from the isotope mass balance by assuming it was generated from the water or carbon dioxide sampled simultaneously.

In cases where the augmentation leads to isotope effects significantly greater than the existing fractionation between original methane precursor and methane, then this approach can be used without the injection of the label.

Possible Modifications and Variations

The main improvement to this method would be in the calculations, and in the determination of water mixing in the reservoir. While the use of samples is reasonable to quantify the label in the water, unusual mixing patterns or spatial separation between the augmentation process and the label could bias the results.

The fractionation factor for methanogenesis needs to be defined for each specific augmentation process.

Also, if a specific augmentation process should stimulate methanogenesis from substrates that do not isotopically equilibrate with water or carbon dioxide, then empirical corrections may be needed to account for the proportion of isotopes in methane originating from these precursors.

Advantages and Improvements

This process fills an emerging need in the natural gas community, namely a method to estimate the success and profitability of augmentation technologies, and a tool to optimize process control in field settings. As such, it is a novel process and would immediately become the state of the art.

Apparatus and Process Description

Figure 2:
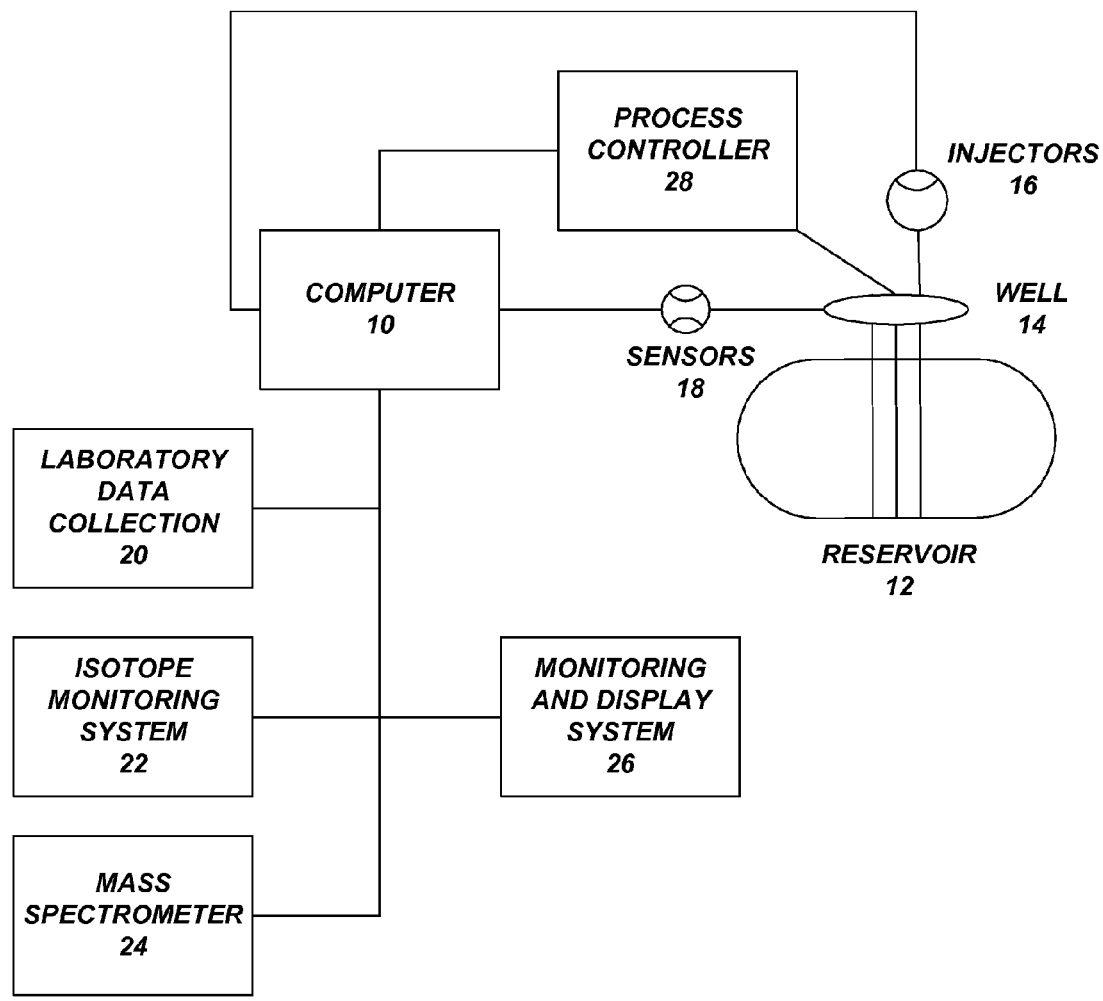
FIG. 2 is a schematic diagram illustrating an apparatus that may be used in performing the process steps according to a preferred embodiment of the present invention.

FIG. 2 is a schematic diagram illustrating an apparatus that may be used in performing the process steps according to a preferred embodiment of the present invention. In this exemplary embodiment, a computer 10 provides for centralized data collection, performs the necessary calculations, provides process control and monitoring, and displays the results for end users. A reservoir 12 includes a well 14, which is coupled to injectors 16 and sensors 18, both of which communicate with and are under the control of the computer 10. Information may also be collected by the computer 10 from laboratory data collection 20, an isotope monitoring system 22, and/or a mass spectrometer 24. Finally, the computer 10 provides feedback and control to a monitoring and display system 26, the injectors 16 and a process controller 28 that controls the operation of the well 14.

Figure 3:
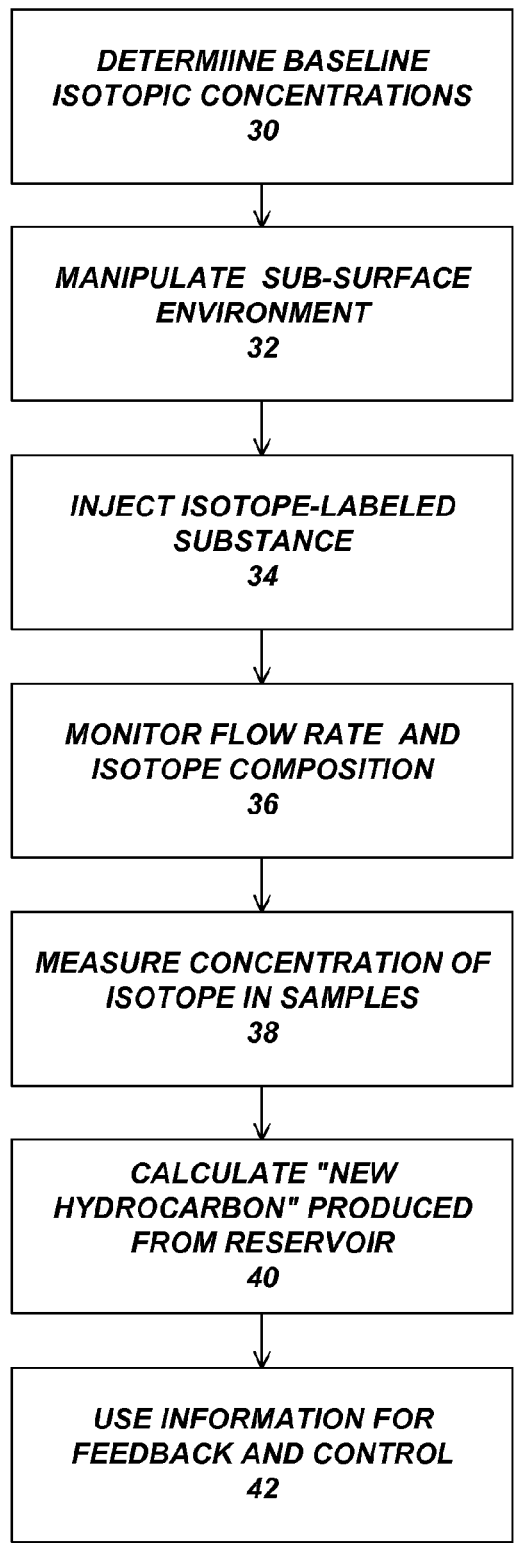
FIG. 3 is a flow chart illustrating the process steps performed using the apparatus of FIG. 2 according to the preferred embodiment of the present invention.

FIG. 3 is a flow chart illustrating the process steps performed using the apparatus of FIG. 2 according to the preferred embodiment of the present invention. These process steps comprise a method for determining the production rate of hydrocarbon (e.g. methane) through biological activity, with a particular application toward bioaugmentation or stimulation of methanogenesis in reservoirs in sub-surface environments.

Block 30 represents the step of determining specific baseline isotopic concentrations for the reservoir.

This step includes measuring a baseline isotope ratio in a hydrocarbon (e.g. methane) pre-existing in the reservoir. Before injection of any labels, baseline samples of gas and water from the reservoir are collected and analyzed for at least one of a specific selected isotopic abundance. In one exemplary implementation, the specific isotopic abundance analyzed is a hydrogen isotope (e.g. deuterium or tritium) to hydrogen ratio. In another exemplary implementation, the specific isotopic abundance analyzed is a carbon isotope (e.g. $^{13}C$ or $^{14}C$) to $^{12}C$ ratio. However, any isotope present in methane could be used for the purposes described. These include stable isotopes, such as carbon 13, and radioisotopes, such as carbon 14 and tritium.

Block 32 represents manipulating the reservoir to facilitate production of new hydrocarbon in the reservoir.

After determination of the baseline isotopic concentrations of the gas and water samples from the reservoir, this step includes manipulating the sub-surface environment to facilitate production of new hydrocarbon (e.g. methanogenesis). The manipulation of the reservoir causes a change in the isotopic composition of a hydrocarbon (e.g. methane) in the reservoir and includes any stimulation, biostimulation, and augmentation technologies. This may include, but is not limited to, an inoculum comprised of a methanogenic microbial community; nutrients to facilitate growth of native organisms; chemicals or enzymes designed to alter or liberate microbial substrates in-situ; or physical processes designed to fracture or heat the reservoir and enhance methanogenic substrates in-situ.

Block 34 represents injecting a substance labeled with the isotope into the reservoir before, in conjunction with or after the manipulation of the reservoir.

The isotope-labeled substance may comprise isotope-labeled water. As indicated earlier, any isotope present in the hydrocarbon could be used for the purposes described herein. In one exemplary implementation, the isotope-labeled water is a hydrogen isotope (e.g. deuterium or tritium) labeled water. In another exemplary implementation, the isotope-labeled water is a carbon isotope (e.g. $^{13}C$ or $^{14}C$) labeled as carbon dioxide, carbonic acid, bicarbonate or carbonate ion. Tritium could be added as a water tracer and used as a label, while carbon 13 and 14 would need to be added as carbon dioxide or an equivalent species (carbonic acid, bicarbonate or carbonate ion).

Various common injection technologies may be used to inject the isotope-labeled water into the reservoir. The amount to be injected depends on the estimated size and water content of the underlying reservoir.

The isotope-labeled water may also be diluted with water pre-existing in the reservoir prior to injection into the reservoir. This reduces the uncertainty in and/or minimizes the dilution of the isotope-labeled water after injection into the reservoir.

Block 36 represents measuring a flux and isotope ratio of the hydrocarbon (e.g. methane) coming from the reservoir.

This step includes measuring the overall hydrocarbon flux from the reservoir and the isotope ratio of the hydrocarbon gas sample. This is achieved by monitoring the selected isotope content of the produced hydrocarbon and the flow rate of the hydrocarbon. In an exemplary implementation, the measurements are made in-situ within the reservoir. In a preferred exemplary implementation, monitoring of the selected isotope content is accomplished in-line with a laser-based isotope monitoring system, using data from the sensors at the well head. In another exemplary implementation, the monitoring is accomplished through the collection of discrete samples at regular intervals (e.g., twice daily) and quantified by determining an isotope ratio using the mass spectrometer. In one exemplary implementation, the isotope ratio of the hydrocarbon is a hydrogen isotope (e.g. deuterium or tritium) to hydrogen ratio. In another exemplary implementation, the isotope ratio of the hydrocarbon is a carbon isotope (e.g. $^{13}C$ or $^{14}C$ to $^{12}C$ ratio.

Block 38 represents measuring the isotope ratio of a hydrocarbon (e.g. methane) precursor in a liquid or vapor sample collected from the reservoir at one or more time periods.

This step includes measuring the concentration of the isotope in a liquid or vapor sample obtained from the reservoir at specified time periods and determining the isotope ratio within the sample at the time periods. The samples are monitored to track the extent of dilution of the isotope-label into the reservoir, and include samples of water, carbon dioxide, carbonic acid, bicarbonate, or carbonate ion, the expected biological precursors to the hydrocarbon. In one exemplary implementation, a hydrogen isotope (e.g. deuterium or tritium) to hydrogen ratio is measured from water obtained from the reservoir. In another exemplary implementation, a carbon isotope (e.g. $^{13}C$ or $^{14}C$) to $^{12}C$ ratio is measured from a $CO_2$ species (e.g. $CO_2$, carbonic acid, bicarbonate or carbonate ion) in liquid or gas samples obtained from the reservoir.

In one exemplary implementation, the monitoring is achieved on-site with a laser-based isotope analyzer, using data from the sensors at the reservoir. In another exemplary implementation, the measurements are made in-situ within the reservoir. In a further exemplary implementation, discrete samples are collected and measured in a laboratory. While the use of samples is reasonable to quantify the isotope-label in the sample, unusual mixing patterns or spatial separation between the augmentation process and the isotope-label could bias the results.

Block 40 represents calculating a flux of the "new hydrocarbon" produced in the reservoir using the information collected in the previous steps and according to an isotope mass balance, as described above.

After the necessary information is collected, this step includes calculating the production of new hydrocarbon (e.g. new methane) in the reservoir for each sampling time interval using, for example, an isotope mass balance approach. The fractionation factor $\alpha$ will need to be determined or estimated for each specific augmentation processes. The fractionation factor $\alpha$ is an effective constant representing both kinetic and equilibrium isotope effects, as well as isotope exchange. In one exemplary implementation, $\alpha$ is the isotope fractionation factor between the water and the new methane. In another exemplary implementation, $\alpha$ is the fractionation factor between a $CO_2$ species (e.g. $CO_2$, carbonic acid, bicarbonate or carbonate ion) in the liquid or vapor and the new methane. In some exemplary implementations, alternative isotope mass balance equations are used to calculate the production of new hydrocarbon.

Block 42 represents using the calculated "new hydrocarbon", as well as the information collected in the previous steps, for feedback and control in various ways. For example, this step may include distinguishing the newly generated hydrocarbon (e.g. newly generated methane) from the pre-existing hydrocarbon (e.g. pre-existing methane) in the reservoir as a mechanism to determine, store and display the sharing or distribution of profits, royalties, revenue, etc., for example, at a monitoring and display system. In another example, this step may include differentiating between newly generated hydrocarbon and pre-existing hydrocarbon as a feedback mechanism, for example, in determining and comparing the efficacy of various facilitation processes to estimate the success and profitability of augmentation technologies, and to control the further operation of the augmentation technologies via a process controller.

REFERENCES

The following references are incorporated by reference herein:

1. Brian J. Campbell, Chao Li, Alex L. Sessions and David L. Valentine, "Hydrogen isotopic fractionation in lipid biosynthesis by $H_2$-consuming *Desulfobacterium autotrophicum*," Geochimica et Cosmochimica Acta, (2009).
2. M. C. Redmond and D. L. Valentine, "Stable Isotopes in Microbial Ecology," Encyclopedia of Microbiology (Moselio Schaechter, Editor), pp. 281-285 Oxford: Elsevier, 2009.
3. J. D. Kessler, W. S. Reeburgh, D. L. Valentine, F. S. Kinnaman, E. T. Peltzer, P. G. Brewer, J. Southon, and S. C. Tyler, "A survey of methane isotope abundance (14C, 13C, 2H) from five near shore marine basins that reveals unusual radiocarbon levels in subsurface waters," Journal of Geophysical Research, Vol. 113, C12021, 2008.
4. Franklin S. Kinnaman, David L. Valentine, and Stanley C. Tyler, "Carbon and hydrogen isotope fractionation associated with the aerobic microbial oxidation of methane, ethane, propane and butane," Geochimica et Cosmochimica Acta, (2006) 71: 271-283.
5. Cameron J. Adams, Molly C. Redmond, and David L. Valentine, "Pure-Culture Growth of Fermentative Bacteria, Facilitated by H2 Removal: Bioenergetics and H2 Production," Applied and Environmental Microbiology, Vol. 72, No. 2, February 2006, p. 1079-1085
6. David L. Valentine, Miriam Kastner, George D. Wardlaw, Xuchen Wang, Alexandra Purdy, and Douglas H. Bartlett, "Biogeochemical investigations of marine methane seeps, Hydrate Ridge, Oreg.," Journal of Geophysical Research, Vol. 110, G02005, 2005.
7. David L. Valentine, Amnat Chidthaisong, Andrew Rice, William Reeburgh, and Stanley C. Tyler, "Carbon and hydrogen isotope fractionation by moderately thermophilic methanogens," Geochimica et Cosmochimica Acta, (2004) 68: 1571-1590.
8. D. L. Valentine, A. L. Sessions, S. C. Tyler, and A. Chidthaisong, "Hydrogen isotope fractionation during $H_2/CO_2$ acetogenesis: hydrogen utilization efficiency and the origin of lipid-bound hydrogen," Geobiology, (2004) 2:179-188.
9. Amnat Chidthaisong, Kuk-Jeong Chin, David L. Valentine, and Stanley C. Tyler, "A comparison of isotope fractionation of carbon and hydrogen from paddy field rice roots and soil bacterial enrichments during $CO_2/H_2$ methanogenesis," Geochimica et Cosmochimica Acta, (2002) 66: 983-995.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method of determining a flux of new methane generated through manipulation of a methane-containing subsurface organic deposit, comprising:
    (a) measuring a baseline isotope ratio ($R_{rm}$) in methane pre-existing in a reservoir;
    (b) manipulating the reservoir to facilitate generation of new methane in the reservoir;
    (c) injecting a substance labeled with the isotope into the reservoir;
    (d) measuring a flux ($F_m$) and isotope ratio ($R_{pm}$) of methane from the reservoir, following the manipulation of the reservoir that facilitates the generation of the new methane;
    (e) measuring an isotope ratio ($R_{pw}$) of a methane precursor in a liquid or vapor sample obtained from the reservoir at one or more periods; and
    (f) calculating a flux ($F_{nm}$) of the new methane from the reservoir according to an isotope mass balance:

$$F_{nm}=F_m\times(R_{pm}-R_{rm})/(\alpha R_{pw}-R_{rm})$$

wherein $\alpha$=isotope fractionation factor between the methane precursor in the liquid or vapor and the new methane.

2. The method of claim 1, wherein the reservoir is manipulated through stimulation.

3. The method of claim 1, wherein the reservoir is manipulated through augmentation.

4. The method of claim 3, wherein the augmentation includes an inoculum comprised of a methanogenic microbial community, nutrients to facilitate growth of native organisms, chemicals or enzymes designed to alter or liberate microbial substrates in-situ, or physical processes designed to fracture or heat the reservoir and enhance methanogenic substrates in-situ.

5. The method of claim 1, wherein the substance labeled with the isotope is diluted with the reservoir's contents prior to injection into the reservoir.

6. The method of claim 1, wherein the isotope is an isotope naturally present in the methane.

7. The method of claim 1, wherein the isotope is deuterium or tritium.

8. The method of claim 7, wherein the isotope is added to the reservoir as labeled water.

9. The method of claim 1, wherein the isotope is carbon 13 or carbon 14.

10. The method of claim 9, wherein the isotope is added to the reservoir as carbon dioxide, carbonic acid, bicarbonate or carbonate ion.

11. The method of claim 1, wherein the manipulation of the reservoir causes any change in the isotopic composition of methane in the reservoir.

12. The method of claim 1, wherein the isotope fractionation factor is an effective constant representing both kinetic and equilibrium isotope effects, as well as isotope exchange.

13. The method of claim 1, wherein alternative isotope mass balance equations are used to calculate the production of new methane.

14. The method of claim 1, wherein measurements are made in-situ within the reservoir.

15. A method of determining a flux of new methane generated through manipulation of a methane-containing reservoir, comprising:
    (a) measuring a baseline hydrogen isotope/hydrogen ratio ($R_{rm}$) in methane pre-existing in the reservoir;
    (b) manipulating the reservoir to facilitate generation of new methane in the reservoir;
    (c) injecting a water labeled with the hydrogen isotope into the reservoir;
    (d) measuring a flux ($F_m$) and hydrogen isotope/hydrogen ratio ($R_{pm}$) of methane from the reservoir, following the manipulation of the reservoir that facilitates the generation of the new methane;
    (e) measuring a hydrogen isotope/hydrogen ratio ($R_{pw}$) of a water obtained from the reservoir at one or more periods; and
    (f) calculating a flux ($F_{nm}$) of the new methane from the reservoir according to an isotope mass balance:

$$F_{nm}=F_m\times(R_{pm}-R_{rm})/(\alpha R_{pw}-R_{rm})$$

wherein $\alpha$=isotope fractionation factor between the water and the new methane.

16. The method of claim 15, wherein the hydrogen isotope is deuterium (D) or tritium (T).

17. A method of determining a flux of new methane generated through manipulation of a methane-containing reservoir, comprising:
    (a) measuring a baseline carbon isotope/carbon-12 ($^{12}C$) ratio ($R_{crm}$) in methane pre-existing in the reservoir;

(b) manipulating the reservoir to facilitate generation of new methane in the reservoir;

(c) injecting a substance labeled with the carbon isotope into the reservoir;

(d) measuring a flux ($F_m$) and carbon isotope/carbon-12 ratio ($R_{cpm}$) of methane from the reservoir, following the manipulation of the reservoir that facilitates the generation of the new methane;

(e) measuring an carbon isotope/carbon-12 ratio ($R_{pc}$) of a $CO_2$ species in a liquid or gas sample obtained from the reservoir at one or more periods; and (f) calculating a flux ($F_{nm}$) of the new methane from the reservoir according to an isotope mass balance:

$$F_{nm}=F_m\times(R_{cpm}-R_{crm})/(\alpha R_{pc}-R_{crm})$$

wherein $\alpha$=fractionation factor between the $CO_2$ species in the liquid or vapor and the new methane.

18. The method of claim 17, wherein the $CO_2$ species is $CO_2$, carbonic acid, bicarbonate or carbonate ion.

19. The method of claim 17, wherein the carbon isotope is carbon-13 ($^{13}C$) or carbon-14 ($^{14}C$).

20. A method of determining a flux of new hydrocarbon generated through manipulation of a subsurface organic deposit, comprising:

(a) measuring a baseline isotope ratio ($R_{rm}$) in hydrocarbons pre-existing in a reservoir;

(b) manipulating the reservoir to facilitate generation of new hydrocarbon in the reservoir;

(c) injecting a substance labeled with the isotope into the reservoir;

(d) measuring a flux ($F_m$) and isotope ratio ($R_{pm}$) of hydrocarbon from the reservoir, following the manipulation of the reservoir that facilitates the generation of the new hydrocarbon;

(e) measuring an isotope ratio ($R_{pw}$) of a hydrocarbon precursor in a liquid or vapor sample obtained from the reservoir at one or more periods; and (f) calculating a flux ($F_{nm}$) of the new hydrocarbon from the reservoir according to an isotope mass balance:

$$F_{nm}=F_m\times(R_{pm}-R_{rm})/(\alpha R_{pw}-R_{rm})$$

wherein $\alpha$=isotope fractionation factor between the hydrocarbon precursor in the liquid or vapor and the new hydrocarbon.

* * * * *